(12) United States Patent
Komatsuki et al.

(10) Patent No.: US 11,225,448 B2
(45) Date of Patent: Jan. 18, 2022

(54) METHOD FOR MANUFACTURING ISOPULEGOL

(71) Applicant: TAKASAGO INTERNATIONAL CORPORATION, Tokyo (JP)

(72) Inventors: Yasuhiro Komatsuki, Kanagawa (JP); Kazuya Taira, Kanagawa (JP); Ayaka Koike, Kanagawa (JP); Kazuki Kimura, Kanagawa (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 17/156,817

(22) Filed: Jan. 25, 2021

(65) Prior Publication Data

US 2021/0238115 A1     Aug. 5, 2021

(30) Foreign Application Priority Data

Jan. 30, 2020    (JP) ............................. JP2020-013700

(51) Int. Cl.
    *C07C 29/14*         (2006.01)
    *C07C 29/38*         (2006.01)
    *C07C 35/17*         (2006.01)

(52) U.S. Cl.
    CPC .............. *C07C 29/14* (2013.01); *C07C 29/38* (2013.01); *C07C 35/17* (2013.01); *C07C 2601/14* (2017.05)

(58) Field of Classification Search
    CPC ...... C07C 29/38; C07C 29/14; C07C 2601/14
    See application file for complete search history.

(56) References Cited

U.S. PATENT DOCUMENTS

| | | |
|---|---|---|
| 6,774,269 B2 | 8/2004 | Iwata et al. |
| 7,550,633 B2 | 6/2009 | Friedrich et al. |
| 7,608,742 B2 * | 10/2009 | Friedrich ................ C07F 5/069 556/181 |
| 8,329,930 B2 | 12/2012 | Itoh et al. |
| 8,329,931 B2 | 12/2012 | Itoh et al. |
| 8,580,991 B2 | 11/2013 | Itoh et al. |
| 2011/0319638 A1 | 12/2011 | Itoh et al. |
| 2015/0315110 A1 | 11/2015 | Itoh et al. |
| 2015/0329452 A1 * | 11/2015 | Itoh ........................ C07B 53/00 568/828 |

OTHER PUBLICATIONS

Itoh et al. (Highly selective aluminum-catalysed intramolecular Prins reaction for L-menthol synthesis, RSC Advances, Nov. 2014, Issue 4, pp. 61619-61623). (Year: 2014).*

* cited by examiner

*Primary Examiner* — Rosalynd A Keys
(74) *Attorney, Agent, or Firm* — Sughrue Mion, PLLC

(57) ABSTRACT

A method for manufacturing isopulegol includes the step of diastereoselective ring-closing a citronellal using an aluminum compound of formula (1) below. In formula (1), X represents a halogen atom, Y represents a halogen atom or a hydrogen atom, and $R_1$ represents a phenyl group or a cycloalkyl group of 5 to 12 carbons.

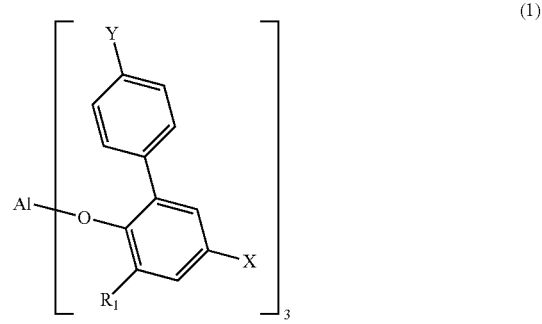

(1)

1 Claim, No Drawings

METHOD FOR MANUFACTURING ISOPULEGOL

CROSS-REFERENCE TO RELATED APPLICATIONS

This application claims priority from Japanese Patent Application No. 2020-013700 filed on Jan. 30, 2020, the entire subject matter of which is incorporated herein by reference.

BACKGROUND OF INVENTION

Technical Field

The present invention relates to a method for manufacturing isopulegol.

Background Art

Isopulegol is common as a cooling agent, and one of the reactions to produce isopulegol is the catalytic ring-closing of citronellal. Due to four diastereomers in isopulegol, it is need a selective ring-closing method to produce isopulegol with highly diastereomer ratio, especially, it is need a catalyst for ring-closing of citronellal in a highly normal ratio.

Recently, for solving the above problem, a synthetic method has been found with highly normal ratio by aluminum catalyst (Patent Documents 1 to 7).

Patent Document 1: US 2015/0315110 A1
Patent Document 2: U.S. Pat. No. 8,329,931 B2
Patent Document 3: U.S. Pat. No. 8,580,991 B2
Patent Document 4: US 2011/0319638 A1
Patent Document 5: U.S. Pat. No. 8,329,930 B2
Patent Document 6: U.S. Pat. No. 7,550,633 B2
Patent Document 7: U.S. Pat. No. 6,774,269 B2

SUMMARY OF INVENTION

However, there was a problem that the synthetic methods described in Patent Documents 1 to 7 have not efficient ability to obtain n-isopulegol with highly normal ratio.

The present invention has been made in light of the above-described conventional situation, and an object of the present invention is to provide a method of efficiently manufacturing n-isopulegol.

The present invention provides the following manufacturing method.

[1] A method for manufacturing isopulegol comprising the step of diastereoselective ring-closing a citronellal using an aluminum compound of formula (1) below:

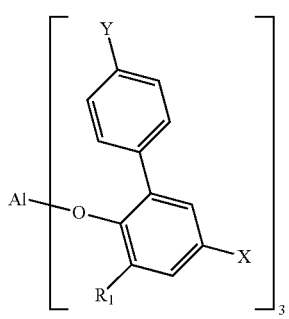

(1)

wherein X represents a halogen atom, Y represents a halogen atom or a hydrogen atom, and $R_1$ represents a phenyl group or a cycloalkyl group of 5 to 12 carbons.

[2] The method for manufacturing isopulegol according to [1], wherein said X is a chlorine atom or a bromine atom.

[3] The method for manufacturing isopulegol according to [1] or [2], wherein said Y is a chlorine atom or a bromine atom.

[4] The method for manufacturing isopulegol according to any one of [1] to [3], wherein said $R_1$ is a cyclohexyl group.

[5] The method for manufacturing isopulegol according to any one of [1] to [4], wherein the step of diastereoselective ring-closing a citronellal is performed in the presence of a β-keto ester or a β-diketone.

[6] The method for manufacturing isopulegol according to [5], wherein the β-keto ester is an acetoacetic acid ester.

With the present invention, n-isopulegol is obtained efficiently and stereoselectively.

DETAILED DESCRIPTION OF THE INVENTION

The method of manufacturing of the present invention includes the step of diastereoselective ring-closing citronellal using an aluminum compound represented by the following formula (1) (sometimes referred to as aluminum compound (1)).

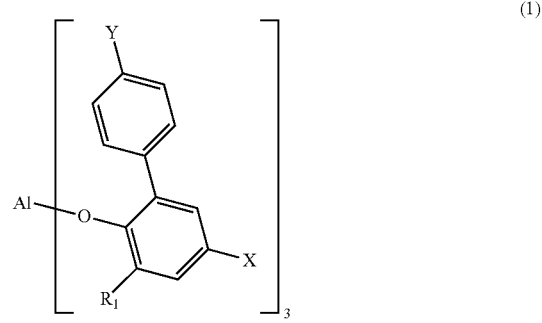

(1)

(In the formula (1), X represents a halogen atom, Y represents a halogen atom or a hydrogen atom, and $R_1$ represents a phenyl group or an alicyclic group of 5 to 12 carbons.)

$R_1$ may be the same or different respectively, X may be the same or different respectively, and Y may be the same or different respectively.

In the process of preparing of the present invention, cyclization from citronellal to isopulegol is smoothly carried out by catalyzing the aluminum compound (1). In addition, such cyclization in the presence of a β-keto ester or β-diketone affords more favorable results.

The aluminum compound (1) is obtained by reacting an aluminum compound represented by the following formula (2) (hereinafter referred to as aluminum compound (2)) with a phenolic compound represented by the following formula (3) (hereinafter referred to as phenolic compound (3)).

$$Al(R_2)_3 \quad (2)$$

(In the formula (2), $R_2$ represents a linear or branched alkyl group having 1 to 8 carbons, or a halogen atom. $R_2$ may be the same or different respectively.)

(3)

$$\text{(structure: benzene ring with } R_1 \text{ and OM at adjacent positions, X at another position, connected to a second phenyl ring bearing Y)}$$

(In the formula (3), $R_1$, X and Y are the same in definition to those in the formula (1), and M represents hydrogen, lithium, sodium or potassium atom.)

$R_2$ in the formula (2) is described as the followings.

Examples of linear or branched alkyl group having 1 to 8 carbons include methyl, ethyl, n-propyl, isopropyl, n-butyl, isobutyl, sec-butyl, tert-butyl, pentyl, hexyl, heptyl, and octyl group. Among these, methyl and ethyl group are preferred.

Examples of the halogen atoms include chlorine atom and bromine atom, provided chlorine atom is preferred.

Each group in the formula (1) or the formula (3) is described as the followings

Examples of the cycloalkyl group having 5 to 12 carbons represented by $R_1$ include a cyclopentyl group, a cyclohexyl group, a cycloheptyl group, a cyclooctyl group, a cyclodecyl group, a cyclododecyl group, a bicyclo[2.2.1]heptyl group, and the like. However, a cyclohexyl group is preferred.

As the halogen atoms represented by X and Y, examples thereof include fluorine atom, chlorine atom and bromine atom, provided chlorine atom and bromine atom are preferred.

As phenolic compound (3) (working in the reaction as a ligand), examples thereof include 4-chloro-2,6-diphenylphenol, 4-bromo-2,6-diphenylphenol, 4-chloro-2-cyclopentyl-6-phenylphenol, 4-bromo-2-cyclopentyl-6-phenylphenol, 4-chloro-2-cyclohexyl-6-phenylphenol, 4-bromo-2-cyclohexyl-6-phenylphenol, 4-chloro-2-cycloheptyl-6-phenylphenol, 4-bromo-2-cycloheptyl-6-phenylphenol, 4-chloro-2-cyclooctyl-6-phenylphenol, 4-bromo-2-cyclooctyl-6-phenylphenol, 4-chloro-2-cyclododecyl-6-phenylphenol, 4-bromo-2-cyclododecyl-6-phenylphenol, and 4-chloro-2-bicyclo[2.2.1]heptyl-6-phenylphenol, 4-bromo-2-bicyclo[2.2.1]heptyl-6-phenylphenol, 4-chloro-2-(decahydro-1,4-methanonaphthyl)-6-phenylphenol, 4-bromo-2-(decahydro-1,4-methanonaphthyl)-6-phenylphenol, 4-chloro-2-cyclohexyl-6-(4'-chlorophenyl)phenol, 4-bromo-2-cyclohexyl-6-(4'-chlorophenyl)phenol, 4-bromo-2-cyclohexyl-6-(4'-bromophenyl)phenol, 4-chloro-2-bicyclo[2.2.1]heptyl-6-(4'-chlorophenyl)phenol, 4-chloro-2-(decahydro-1,4-methanonaphthyl)-6-(4'-chlorophenyl)phenol and the like, or lithium phenoxide, sodium phenoxide and potassium phenoxide thereof.

Among these, 4-chloro-2-cyclohexyl-6-phenylphenol, 4-bromo-2-cyclohexyl-6-phenylphenol, 4-chloro-2-cyclohexyl-6-(4'-chlorophenyl)phenol, 4-chloro-2-(decahydro-1,4-methanonaphthyl)-6-phenylphenol and its sodium phenoxide thereof are preferred.

The phenolic compound (3) can be synthesized by common synthetic methods.

The aluminum compound (1) is obtained by reacting the aluminum compound (2) with the phenolic compound (3).

The phenolic compound (3) may be reacted at a ratio of preferably 3.0 to 5.0 equivalents, more preferably 3.0 to 3.5 equivalents, with respect to a 1.0 equivalent amount of the aluminum compound (2).

The reaction can be carried out in an inert gas atmosphere or in the presence of an inert solvent.

For example, nitrogen, argon, other rare gases, and the like are preferably used as the inert gas.

Examples of the inert solvent include aliphatic hydrocarbon (hexane, heptane, etc.), alicyclic hydrocarbon (cyclohexane, methylcyclohexane, etc.), aromatic hydrocarbon (toluene, xylene, etc.), ether (diethyl ether, diisopropyl ether, tetrahydrofuran, etc.), halogenated hydrocarbon (dichloromethane, dichloroethane, etc.), and the like. Preferred among these are aliphatic or aromatic hydrocarbon, with toluene or heptane being more preferred. Preferably, these solvents are predried or an anhydrous solvent is used.

The amount of solvent used (L: litter) is preferably in the range of 1 to 1000 times (L/kg) the amount of use (kg: kilogram) of the phenolic compound (3), and more preferably in the range of 10 to 400 times (L/kg) the amount of use.

The reaction temperature is preferably in the range of about $-30°$ C. to $100°$ C. and preferably in the range of about $-10°$ C. to $70°$ C. With respect to reaction time, by performing the reaction at preferably from about 0.25 to 30 hours, more preferably from about 0.5 to 10 hours, while maintaining the aforementioned temperature, smooth production of the aluminum compound (1) as catalyst is possible.

The method of manufacturing of the present invention is preferably carried out under an inert gas atmosphere, such as nitrogen gas or argon gas, under non-solvent conditions or in the presence of an inert solvent by adding citronellal to the aluminum compound (1) as the catalyst obtained above.

Additionally, in the method of manufacturing of the present invention, it is preferable to prepare the aluminum compound (1) by mixing in advance the aluminum compound (2) and the phenolic compound (3), and then add citronellal.

Examples of the inert solvent used include aliphatic hydrocarbon (hexane, heptane, octane, etc.), alicyclic hydrocarbon (cyclohexane, methylcyclohexane, etc.), aromatic hydrocarbon (benzene, toluene, xylene, etc.), ether (diethyl ether, diisopropyl ether, dimethoxyethane, methyl tert-butyl ether, tetrahydrofuran, dioxane, dioxolane, etc.), or halogenated hydrocarbon (dichloromethane, dichloroethane, chlorobenzene), and the like. Preferred among these are organic solvents such as toluene or heptane. Preferably, these solvents are predried or an anhydrous solvent is used.

The amount used (L: litter) of these solvents is preferably 0 to 20 times (L/kg) compared to the amount used (kg: kilogram) of citronellal, and more preferably in the range of 0.5 to 7 times (L/kg).

In the above reaction, β-keto ester or β-diketone represented by the following formula (4) may be added.

(4)

$$\text{(structure: } R_3\text{-C(=O)-CH}_2\text{-C(=O)-}R_4\text{)}$$

(In the formula (4), $R_3$ represents a linear or branched alkyl having 1 to 4 carbon atoms which may be substituted, cyclohexyl, or benzyl group, and $R_4$ represents a linear or branched alkyl group having 1 to 4 carbon atoms, a linear or branched alkoxy group having 1 to 4 carbon atoms, or cyclohexyloxy group.)

In $R_3$ and $R_4$, examples of the linear or branched alkyl groups having 1 to 4 carbon atoms include methyl, ethyl, n-propyl, isopropyl, n-butyl, isobutyl, sec-butyl, and tert-butyl group. Among these, methyl and ethyl group are preferable.

In $R_4$, examples of the linear or branched alkoxy groups having 1 to 4 carbon atoms include methoxy group, ethoxy group, n-propoxy group, isopropoxy group, n-butoxy group, isobutoxy group, sec-butoxy group, and tert-butoxy group. Among these, methoxy group and ethoxy group are preferable.

In $R_3$, examples of substituents of the linear or branched alkyl groups having 1 to 4 carbon atoms include halogen atoms such as chlorine and bromine atoms, alkoxy group such as methoxy group and ethoxy group, benzyloxy group, and the like.

Examples of preferred β-ketoesters or β-diketones include, for example, the following compounds.

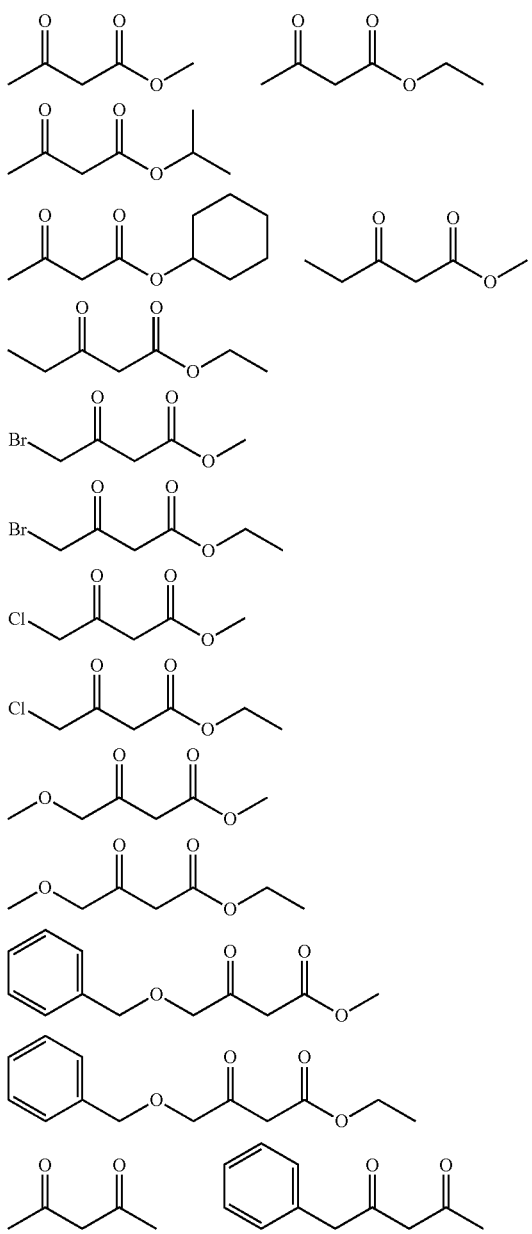
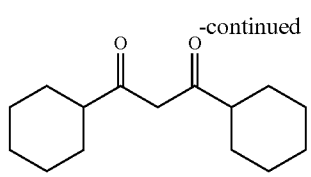

In these compounds, methyl acetoacetate and ethyl acetoacetate are more preferable.

Also, the use amount (moles) of the β-keto ester or the β-diketone represented by the formula (4) is preferably within the range of 0 to 1.0 times and more preferably within the range of 0.05 to 0.5 times the use amount (moles) of the phenolic compound (3).

EXAMPLES

Although the present invention will be described in detail with reference to examples and comparative examples, the present invention is not limited thereto.

The products in the Examples and Comparative Examples were measured using the following apparatus.

Gas chromatography (GC): GC-2011 gas chromatography (Shimadzu Corporation)

Capillary Column: DB-WAX (30 m×0.50 μm×0.32 mm ID) (Agilent Technology)

The conversion rate (conversion rate of citronellal), the selection rate (selection rate of isopulegol in the obtained compound), and the n-selection rate (selection rate of n-isopulegol in the obtained isopulegol) are calculated as follows.

Conversion rate (%)={1−[(chromatogram area of unreacted citronellal remaining in the reaction solution)/(sum of chromatogram area of unreacted citronellal and total reaction product remaining in the reaction solution)]×100}

Selection rate (%)=(chromatogram area of isopulegol/chromatogram area of total reaction product)×100

$n$-Selectivity (%)=(area of chromatogram of $n$-isopulegol/area of chromatogram of isopulegol)×100

Synthesis of Phenol Compound (3)

(Preparation Example 1) Synthesis of 4-chloro-2-cyclohexyl-6-phenylphenol (Cl-CPP)

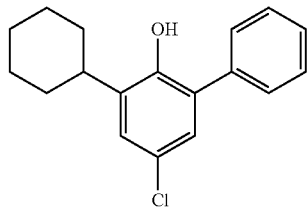 [SMILES: Oc1c(-c2ccccc2)cc(Cl)cc1C1CCCCC1]

2-cyclohexyl-6-phenylphenol (hereinafter referred to as CPP), 5.05 g (20 mmol), 7.60 g (40 mmol) of p-toluenesulfonic acid monohydrate, 2.67 g (20 mmol) of N-chlorosuccinimide, and 200 mL of acetonitrile were added to the 300 mL round bottle flask and stirred at room temperature. After the solvent was evaporated, the residue was washed with 200 mL of toluene and 20 mL of water three times, then purified by silica gel column chromatography (hexane:toluene=4:1) to give 5.49 g of the title compound (95.7% yield).

(Preparation Example 2) Synthesis of 4-bromo-2-cyclohexyl-6-phenylphenol (Br-CPP)

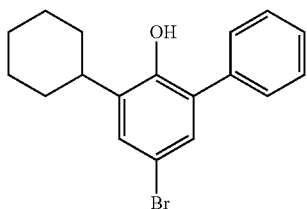 [SMILES: Oc1c(-c2ccccc2)cc(Br)cc1C1CCCCC1]

32.24 g (0.128 mol) of CPP and 320 mL of acetonitrile were added to a 500 mL four-neck flask and dissolved at room temperature. Subsequently, 22.74 g (40 mmol) of N-bromosuccinimide was added divided three times. After stirring for 1 hour, the solvent was evaporated and 200 mL hexane was added to the residue. The residue was filtered and washed twice with 100 mL water. To the resulting residue was added 87 mL of heptane and allowed to stand overnight at −20° C. Filtration of the precipitated solid gave 30.62 g (72.2% yield) of the title compound.

(Preparation Example 3) Synthesis of 4-chloro-2-cyclohexyl-6-(4'-chlorophenyl)phenol (DiCl-CPP)

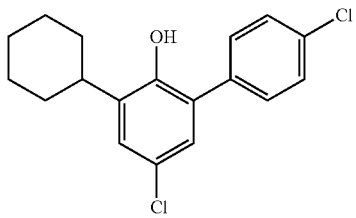 [SMILES: Oc1c(-c2ccc(Cl)cc2)cc(Cl)cc1C1CCCCC1]

In a nitrogen atmosphere, 2.35 g (15 mmol) of 4-chlorophenylboric acid, 12.2 mg (0.05 mmol) of palladium acetate, and 2.90 g (10 mmol) of 2-bromo-4-chloro-6-cyclohexylphenol were added to a 50 mL four necked flask. Subsequently, 20 mL of degassed distilled water and 2.02 g (20 mmol) of diisopropylamine were added and the bath temperature was heated to 100° C. After 1 hour, the conversion ratio was 100% and the selective ratio was 85.9%. To the reaction mixture was added 50 mL of toluene and the organic layer was separated, then the solvent was evaporated to give 3.386 g of crude product. Purification by silica gel column chromatography (hexane:toluene=10:1) gave 2.61 g (99.0% GC purity) of the title compound (81.3% yield).

(Preparation Example 4) Synthesis of 4-chloro-2-cyclohexyl-6-(4'-methoxyphenyl) phenol (Cl-MeO-CPP)

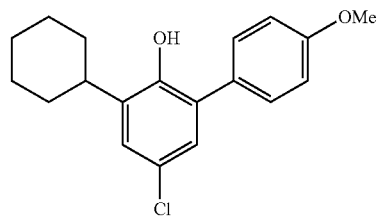 [SMILES: COc1ccc(-c2cc(Cl)cc(C3CCCCC3)c2O)cc1]

In a nitrogen atmosphere, 1.67 g (11 mmol) of 4-methoxyphenylboric acid, 12.0 mg (0.05 mmol) of palladium acetate, and 2.90 g (10 mmol) of 2-bromo-4-chloro-6-cyclohexylphenol were added to a 50 mL four necked flask. Subsequently, 20 mL of degassed distilled water and 2.02 g (20 mmol) of diisopropylamine were added and the bath temperature was heated to 100° C. After 4 hours, the conversion ratio was 100% and the selection ratio was 89.2%. To the reaction was added 50 mL of toluene and the organic layer was separated, then the solvent was evaporated to give 3.69 g of crude product. Purification by column chromatography on silica gel (hexane:toluene=5:1) gave 2.68 g (100% GC purity) of the title compound (84.6% yield).

[Synthesis of Isopulegol]

Isopulegol was synthesized and conversion ratio, selective ratio, and n-selective ratio were determined by the methods described below. The results are given in Table 1.

Example 1

In a nitrogen atmosphere, Cl-CPP 457.8 mg (1.6 mmol) and 50 mL of dehydrated toluene were added to a 100 mL four necked flask. 0.5 mL (0.5 mmol) of triethylaluminum toluene solution (1 mol/L) was added at 15° C.-25° C. and stirred at 40° C. for 2 hours. After cooling to 25° C., a mixture of 7.71 g (50 mmol) of d-citronellal and 26.8 mg (0.23 mmol) of methyl acetoacetate was added dropwise over 30 minutes while holding at the same temperature. After stirring at the same temperature for 1 hour, GC analysis was performed.

Comparative Example 1

The same procedure as Example 1 was performed except that CPP 457.8 mg (1.8 mmol) was used instead of Cl-CPP 457.8 mg (1.6 mmol).

Example 2

The same procedure as in Example 1 was performed except that Br-CPP was used instead of Cl-CPP.

Example 3

In a nitrogen atmosphere, DiCl-CPP 514 mg (1.6 mmol) and 50 mL of dehydrated toluene were added to a 100 mL four necked flask. 0.5 mL (0.5 mmol) of triethylaluminum toluene solution (1 mol/L) was added at 15° C.-25° C. and stirred at 40° C. for 2 hours. After cooling to 25° C., 7.71 g (50 mmol) of d-citronellal was added dropwise over 30 minutes holding at the same temperature. After stirring at the same temperature for 1 hour, GC analysis was performed.

Example 4

The same procedure as in Example 1 was performed except that Cl-MeO-CPP was used instead of Cl-CPP.

Example 5

The same procedure as in Example 1 was performed except that 15.4 g (100 mmol) of d-citronellal was used instead of 7.71 g (50 mmol) of d-citronellal.

Example 6

The same procedure as in Example 3 was performed except that 15.4 g (100 mmol) of d-citronellal was used instead of 7.71 g (50 mmol) of d-citronellal.

Example 7

The same procedure as in Example 5 was performed except that Br-CPP was used instead of Cl-CPP.

Example 8

In a nitrogen atmosphere, to a 100 mL four necked flask, 331 mg (1.0 mmol) of Br-CPP and 15.4 mL of dehydrated toluene were added to a 100 mL four necked flask. 0.3 mL (0.3 mmol) of triethylaluminum toluene solution (1 mol/L) was added at 15° C.-25° C. and stirred at 40° C. for 2 hours. After cooling to −10° C., a mixture of 15.4 g (100 mmol) of d-citronellal and 16.2 mg (0.14 mmol) of methyl acetoacetate were added dropwise over 30 minutes while holding at the same temperature. GC analysis was performed after reactions for 1 and 3 hours at the same temperature.

Example 9

In a nitrogen atmosphere, 212 mg (0.64 mmol) of Br-CPP and 7.77 mL of dehydrated toluene were added to a 100 mL four necked flask. 0.2 mL (0.2 mmol) of triethylaluminum toluene solution (1 mol/L) was added at 15° C.-25° C. and stirred at 40° C. for 2 hours. After cooling to −10° C., a mixture of 15.4 g (100 mmol) of d-citronellal and 10.7 mg (0.092 mmol) of methyl acetoacetate was added dropwise over 30 minutes while holding at the same temperature. GC analysis was performed after reactions for 1 and 3 hours at the same temperature.

Example 10

In a nitrogen atmosphere, 2.65 g (8.0 mmol) of Br-CPP and 38.6 mL of toluene were added to a 100 mL four-neck flask. Then 2.5 mL (2.5 mmol) of a solution of triethylaluminum toluene (1 mol/L) was added and stirred at 40° C. for 2 hours. The internal temperature was cooled to 1° C. in an ice bath. A mixture of 38.6 g (250 mmol) d-citronellal and 134.0 mg (1.15 mmol) methyl acetoacetate were then added dropwise at 5° C. or below. After completion of dropping, GC analysis was performed 30 minutes later, and after confirming the conversion ratio of 99.9%, 1.16 g of water was added, stirred, and allowed to stand overnight at room temperature.

A Vigreux distiller was equipped and 40 mL of toluene was collected under reduced pressure at a bath temperature of 65° C., followed by distillation at a bath temperature of 90° C.-130° C. at 2.0 torr to obtain 36.9 g of isopulegol (isopulegol selectivity 99.7%, n-selectivity 99.4%).

Example 11

To the distillate of Example 10 was added 20 mL of toluene, washed twice with 5% aqueous sulfuric acid and twice with water. Toluene was evaporated to give 2.90 g of crude Br-CPP. Then, 5.7 mL of methanol was added to dissolve the crude product, cooled to −7° C., and the precipitated crystals were filtered. After drying, 2.38 g (97% GC purity) of Br-CPP was obtained as pale yellow crystals.

In a nitrogen atmosphere, 530 mg (1.6 mmol) of Br-CPP obtained above and 8 mL of toluene were added to a 50 mL four necked flask. Then 0.5 mL (0.5 mmol) of a solution of triethylaluminum toluene (1 mol/L) was added and cooled to an internal temperature of 1° C. in an ice bath. A mixture of 23.1 g (150 mmol) of d-citronellal and 134.0 mg (1.15 mmol) of methyl acetoacetate was added dropwise at 5° C. or below. After completion of dropping, GC analysis was performed 30 minutes later, and after confirming the conversion ratio of 99.9%, 1.16 g of water was added, stirred, and allowed to stand overnight at room temperature.

Toluene was evaporated, followed by distillation under reduced pressure at a bath temperature of 90° C.-130° C. to obtain 22.2 g of isopulegol (isopulegol selectivity 99.4%, n-selectivity 99.5%).

Example 12

In a nitrogen atmosphere, 25.0 g (50 mmol) of Br-CPP, 8.47 g (75.5 mmol) of potassium-tert-butoxide, 500 mL of dehydrated toluene were added to the 1 L four necked flask. After refluxing at a bath temperature of 130° C. (internal temperature of 109° C.) for 1 hour, the reaction was cooled to room temperature and filtered under a stream of nitrogen. The cake was washed with 100 mL of toluene to afford 25.7 g (92.3% yield) of Br-CPP potassium salt.

To a 200 mL 3-neck flask was added 1.54 g (6.8 mmol %) of Br-CPP potassium salt obtained above and 45 mL of xylene, and 162 mg (2.0 mol %) of anhydrous aluminum chloride was added at room temperature, and the mixture was heated and stirred at 65° C. for 2.5 hours at an internal temperature of 60° C. and 65° C.

37 wt % of the reaction solution was transferred to a 50 mL Schlenk flask, and after an internal temperature of 15° C., 3.56 g (23.1 mmol) of d-citronellal was added dropwise over 30 minutes. After instillation, GC analysis was performed 2 hours later to confirm the formation of l-n-isopulegol with a conversion ratio of 95.1%, isopulegol selective ratio of 90.9%, and n-selective ratio of 98.7%.

TABLE 1

|  |  | Conversion Ratio (%) | Selective Ratio (%) | n-Selective Ratio (%) |
|---|---|---|---|---|
| Example 1 |  | 99.5 | 99.3 | 98.8 |
| Comparative Example 1 |  | 43.1 | 71.3 | 97.8 |
| Example 2 |  | 99.9 | 99.7 | 99.1 |
| Example 3 |  | 99.9 | 98.7 | 98.9 |
| Example 4 |  | 99.3 | 99.2 | 98.8 |
| Example 5 |  | 84.1 | 99.8 | 99.0 |
| Example 6 |  | 95.6 | 99.0 | 99.0 |
| Example 7 |  | 99.9 | 99.9 | 99.4 |
| Example 8 | 1 hour after | 85.8 | 99.9 | 99.2 |
|  | 3 hours after | 97.6 | 99.9 | 99.5 |
| Example 9 | 1 hour after | 78.3 | 99.6 | 99.3 |
|  | 3 hours after | 97.0 | 99.8 | 99.5 |
| Example 10 |  | 99.9 | 99.7 | 99.4 |
| Example 11 |  | 99.9 | 99.4 | 99.5 |
| Example 12 |  | 95.1 | 90.9 | 98.7 |

The invention claimed is:

1. A method for manufacturing isopulegol comprising a step of diastereoselective ring-closing a citronellal using an aluminum compound of formula (1) below:

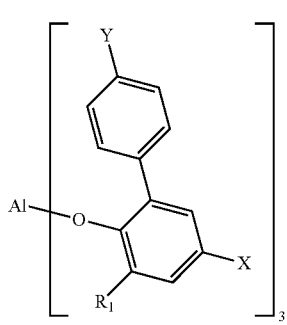 (1)
wherein X is a chlorine atom or a bromine atom,
Y is a chlorine atom or a hydrogen atom, and
R$_1$ is a cyclohexyl group, wherein the step of diastereoselective ring-closing a citronellal is performed in the presence of methyl acetoacetate.
* * * * *